United States Patent [19]

Jessel, Jr. et al.

[11] Plant 4,908

[45] Oct. 26, 1982

[54] CHRYSANTHEMUM PLANT

[76] Inventors: Walter H. Jessel, Jr., 639 Summit St., P.O. Box 112, Doylestown, Ohio 44230; William E. Duffett, 2632 Ira Rd., Akron, Ohio 44313; Marvin D. Mix, P.O. Box 308, Bend, Oreg. 97701

[21] Appl. No.: 232,393

[22] Filed: Mar. 7, 1972

[51] Int. Cl.[3] ..... A01H 5/00

[52] U.S. Cl. ..... Plt./79

[58] Field of Search ..... Plt./82, 79

*Primary Examiner*—Robert E. Bagwill

*Attorney, Agent, or Firm*—Chernoff & Vilhauer

[57] ABSTRACT

A chrysanthemum plant originating as a sport of Bronze Princess Anne, characterized by its reddish-bronze blossoms.

No Drawings

The present invention comprises a new and distinct cultivar of chrysanthemum plant which to the best of its discoverer's knowledge and belief is a sport of the unpatented cultivar known in the United States as Bronze Princess Anne.

The new cultivar is similar in many respects to another cultivar, closely related in color and other characteristics, known as Gay Anne, having the same characteristics of:

1. Plant habit.
2. Flower size.
3. Flower form.
4. Flowering response.
5. Foliage size, color and shape.

The new cultivar is distinguished from Gay Anne by the following characteristics:

1. More intense flower color, with more red tones.
2. Fades more slowly.
3. Faded color more attractive.

The new cultivar differs from related varieties such as Bronze Princess Anne, Gay Anne, SR Bronze Princess Anne, Sweet Anne and Red Anne particularly by its distinctive copper red flower color.

The variety additionally differs from Red Anne in having smooth petals compared to the notched petals of the former.

The new cultivar was discovered in a cultivated area in Bend, Oreg., as a flowered plant, and when asexually reproduced by cuttings at Barberton, Ohio, has been found to retain its distinctive characteristics through successive propagations.

The new cultivar when grown in the vicinity of Barberton, Ohio, has a response period of approximately ten weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States, including coastal California, is from mid-September through May; and in Florida, from December through April.

The accompanying photographic drawing shows the unique characteristics of the new cultivar, the color being as nearly true as possible with color illustrations of this type. In the following description, color references are made to the Munsell Color Book, 1963 edition, except where indicated as Maerz & Paul, "Dictionary of Color", second edition, and comparisons are made with the closely related cultivar Gay Anne shown on the right in the drawing. Where only a single value or description appears for the new cultivar, the same value of description applies as well to the parent cultivar.

BOTANICAL CLASSIFICATION: *Chrysanthemum morifolium*

| | Copper Anne | Gay Anne |
|---|---|---|
| BLOOM: | | |
| Size | 5" | |
| Fully expanded | 5½" | |
| Borne | singly on disbudded stems | |
| Stems | strong | |
| form | decorative | |
| permanence | 10–12 days | |
| color | | |
| center of flower | yellow 10YR7/10 | yellow, 2.5Y8/8 |
| base of petals | lt. yellow 5Y8.5/8 | lt. yellow 5Y8.5/8 |
| inside of petals | bronze to copper red, Maerz & Paul, plates 9,I-7 occasionally having more red tones | orange bronze, 3.75YR5/12 to buff, 2.5Y8.5/4 |

-continued

| BOTANICAL CLASSIFICATION: *Chrysanthemum morifolium* | Copper Anne | Gay Anne |
|---|---|---|
| reverse of petals | slightly darker than the inside of petals | orange yellow, 2.5Y8/8 to buff 10YR8/4 |
| tonality from a distance | copper red | dark bronze to pale buff |
| discoloration | copper bronze, 10YR7/10 | buff, 2.5Y8.5/4 |
| PETALS: | | |
| texture | smooth | notched |
| appearance and form | tubular to open at base, broaden quickly to wide shallow keel, tapering to notched blunt point | |
| arrangement | composite, whorled on a single receptacle | |
| persistance | resist shatter | |
| fragrance | typical chyrsanthemum | |
| REPRODUCTIVE ORGANS: | | |
| stamen, anthers | none–10 | |
| pollen | none–very scant | |
| arrangement | clustered in center of flower, if present | |
| styles | present both ray and disc florets | |
| length | short | |
| ovaries | at the base of petal attached to receptacle | |

-continued

| BOTANICAL CLASSIFICATION: *Chrysanthemum morifolium* | Copper Anne | Gay Anne |
|---|---|---|
| PLANT: | | |
| form | herbaceous | |
| growth | semi-upright | |
| height | 12"–16" | |
| spread | 6"–8" | |
| FOLIAGE: | | |
| top side | dark green, 7.5GY3/4 | |
| size | 6½" long, 4½" wide | |
| quantity | numerous | |
| shape | spatulate lobed | |
| texture | smooth | |
| ribs and veins | prominent | |
| edge | moderately indented | |
| serration | moderate serration | |
| under side | light green, 7.5GY5/4 | |
| stipules | rudimentary | |

We claim:

1. A new and distinct cultivar of chrysanthemum characterized particularly as to uniqueness when compared to the parent cultivar bronze Princess Anne and its closely related cultivar Gay Anne by its more intense flower color, with more red tones, its relatively slower fading characteristic, and its more attractive flower color when faded.

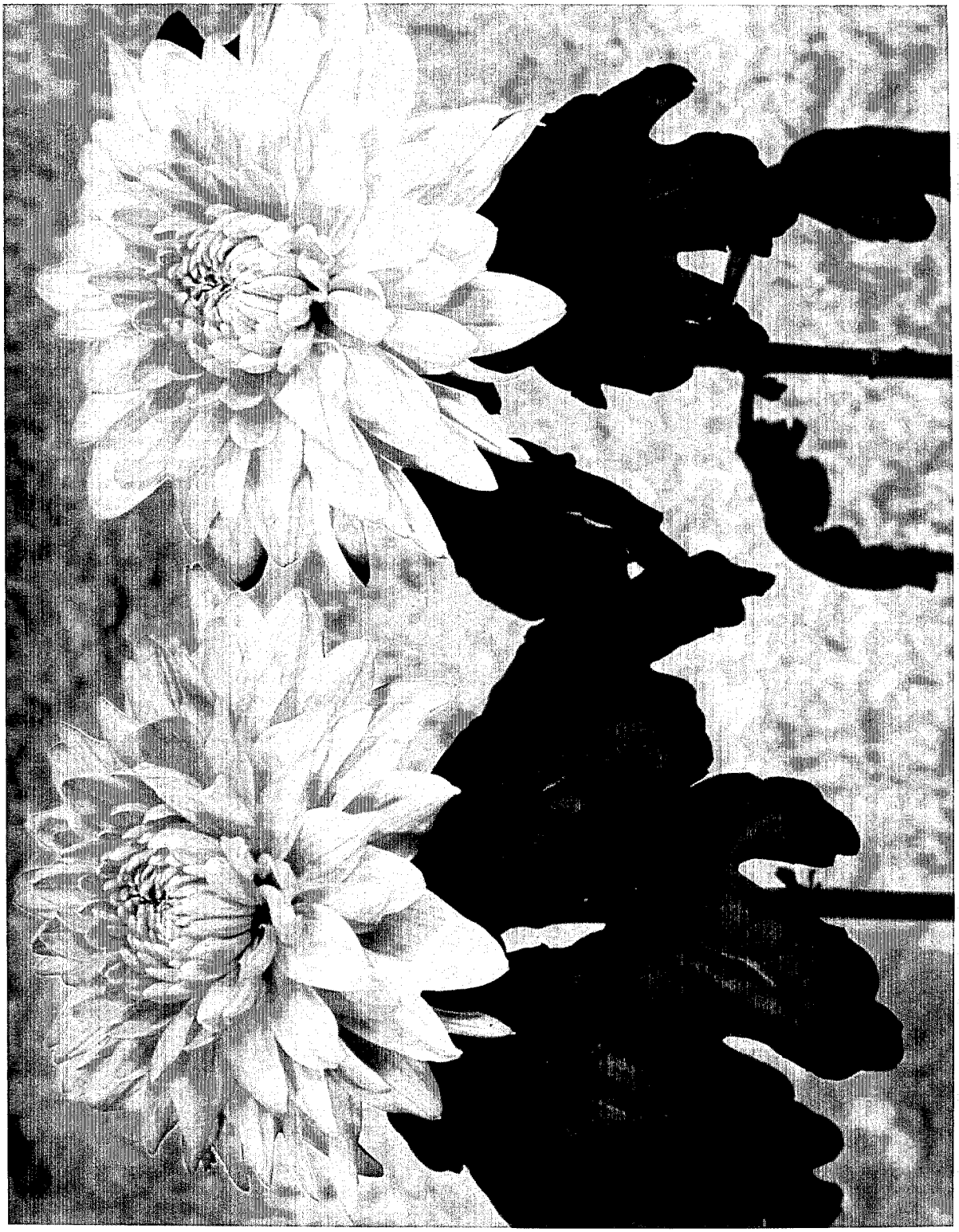

* * * * *